United States Patent
Whelan

Patent Number: 5,918,604
Date of Patent: Jul. 6, 1999

[54] METHOD OF LOADING TENDONS INTO THE KNEE

[75] Inventor: Jeffery M. Whelan, Sugarland, Tex.

[73] Assignee: Arthrex, Inc., Naples, Fla.

[21] Appl. No.: 09/015,618

[22] Filed: Jan. 29, 1998

Related U.S. Application Data

[60] Provisional application No. 60/037,610, Feb. 12, 1997.

[51] Int. Cl.$^6$ .............................. A61B 19/00; A61B 17/58
[52] U.S. Cl. .............................. 128/898; 606/99; 606/72; 623/13; 623/18
[58] Field of Search .................................. 606/72, 96, 98, 606/99; 128/897, 898; 623/11, 13, 18, 20

[56] References Cited

U.S. PATENT DOCUMENTS

| | | | |
|---|---|---|---|
| 4,985,032 | 1/1991 | Goble | 606/96 |
| 5,098,435 | 3/1992 | Stednitz et al. | 606/73 |
| 5,266,075 | 11/1993 | Clark et al. | 623/13 |
| 5,350,380 | 9/1994 | Goble et al. | 606/80 |
| 5,354,300 | 10/1994 | Goble et al. | 606/80 |
| 5,356,413 | 10/1994 | Martins et al. | 606/75 |
| 5,393,302 | 2/1995 | Clark et al. | 623/13 |
| 5,397,356 | 3/1995 | Goble et al. | 623/13 |
| 5,423,823 | 6/1995 | Schmieding | 606/80 |
| 5,431,651 | 7/1995 | Goble | 606/73 |
| 5,562,671 | 10/1996 | Goble et al. | 606/73 |
| 5,601,562 | 2/1997 | Wolf et al. | 606/86 |

*Primary Examiner*—Mickey Yu
*Assistant Examiner*—Dinh X. Nguyen
*Attorney, Agent, or Firm*—Ostrolenk, Faber, Gerb & Soffen, LLP

[57] ABSTRACT

A surgical method for loading ligament grafts into a joint. A longitudinal socket formed in a bone is intersected by a transverse pin. A flexible strand is drawn with the pin through the bone. A looped portion of the strand is diverted so as to protrude out of the entrance to the longitudinal socket. The ends of the strand remaining accessible on either side of the bone. The ligament graft is captured within the strand loop protruding from the entrance to the socket. The strand is retracted into the socket, drawing the graft into the socket by pulling on the accessible ends of the flexible strand. The graft is fixed in the socket using a transverse implant.

15 Claims, 8 Drawing Sheets

5,918,604

METHOD OF LOADING TENDONS INTO THE KNEE

This application claims the benefit of U.S. provisional application Ser. No. 60/037,610, filed Feb. 12, 1997.

BACKGROUND OF THE INVENTION

1. Field of the Invention

The present invention relates to reconstruction of the anterior cruciate ligament (ACL), and, more specifically, to surgical graft fixation using semitendinosus and gracilis tendon autografts.

2. Description of the Related Art

When a ligament or tendon becomes detached from associated bone, surgery usually is required to re-secure the ligament or tendon. Often, a substitute ligament, or graft, is attached to the bone to facilitate re-growth and permanent attachment. Various methods of ligament graft attachment are known, including staples, suture over buttons, and interference screw fixation.

Various problems exist with the known fixation methods. Staples and suture buttons are disadvantageous because they often do not provide fixation sufficient to withstand the normal tensile loads. With suture button fixation, for example, a strand of suture couples the button and the substitute ligament. This strand becomes the "weakest link in the chain," and if the strand breaks, the ligament detaches.

A stronger graft attachment can be obtained by interference screw fixation, whereby an interference screw is used to wedge a graft bone block to the wall of a graft tunnel. See, e.g., U.S. Pat. Nos. 5,211,647, and 5,603,716, incorporated herein by reference.

Although interference screw attachment is more secure than using staples or suture buttons, it is sometimes neither possible nor desirable to provide such fixation, particularly in the femoral tunnel. In revision situations, for example, where a previous reconstruction has been performed, placing a second femoral tunnel placed close to the previous tunnel may not be indicated.

In other cases, a semitendinosus graft must be used because the previous reconstruction used the mid third patellar tendon. Although a bone-semitendinosus graft-bone construct may be prepared using a workstation as disclosed in U.S. Pat. No. 5,397,357, such a procedure is time consuming, and may be undesirable for other reasons.

A fixation technique which provides strong attachment of a semitendinosus graft in the femoral tunnel, using a transverse implant, is disclosed in U.S. Pat. No. 5,601,562, of common assignment with the present application, and incorporated herein by reference. The transverse implant is inserted through a loop in a tendon graft. A threaded portion of the implant screws into the bone as the implant is advanced with rotation into the repair site. The technique is disadvantageous, however, because the graft can become wrapped around the implant as it is rotated. An improved bone implant is the subject of a co-pending U.S. patent application, attorney docket no. P/1493-155.

In addition, the prior art technique noted above requires a forked insertion tool, and a large femoral tunnel is needed to accommodate the forked insertion tool. As a result, the large femoral tunnel undesirably allows the graft to slide laterally, or "wipe" back and forth, along the fixation implant. Moreover, the diameter of the implant necessarily is limited by the size of the opening in the forked insertion tool.

As a further disadvantage, the technique also requires the extra steps of forming and wedging a bone plug into the femoral tunnel after insertion of the ligament. Moreover, the technique does not accommodate a closed-loop graft construct, since the graft must have a free end in order to be inserted with the forked insertion tool. Further, the technique may not be indicated in revision procedures.

Various endoscopic techniques and instruments relating to graft fixation are known in the prior art and can be used in the practice of the present invention. U.S. Pat. No. 5,320,636 to Schmieding discusses an endoscopic drill guide for graft tunnel location. U.S. Patent No. Des. 378,780 illustrates a cannulated headed reamer as can be used in femoral socket formation. U.S. Pat. Nos. 5,269,786 and 5,350,383 disclose drill guides for location of bone tunnels.

The need exists for fixation techniques that utilize narrower femoral/tibial tunnels, to prevent wiping, and that do not require the insertion of bone plugs. Also, the need exists for graft ligament loading techniques that can accommodate closed-looped grafts, that do not require specialized insertion tools to load the graft into the knee, and that can be indicated in certain revision procedures.

SUMMARY OF THE INVENTION

The present invention overcomes the problems of the prior art and fulfills needs such as those noted above by providing a surgical method for loading tendon grafts into a joint and fixating the grafts using a transverse, intraosseous implant. The inventive technique advantageously uses narrow tibial and femoral tunnels, and eliminates the use of sutures, tapes, or extra-osseous metal fixation devices. The procedure also is indicated for revisions that would otherwise be jeopardized by secondary femoral tunnel creation. In addition, the technique can be implemented using a transverse implant that is advanced by impaction into the bone.

As applied in the knee, the method includes the use of standard techniques to drill a longitudinal tunnel in the tibia. Subsequently, a femoral socket is formed, preferably in the lateral femoral condyle. According to the present invention, forming the socket is preferred to forming a tunnel through the lateral femoral cortex. Advantageously, the diameters of the tibial tunnel and femoral socket are made just large enough to accommodate the graft in a snug fit.

A tunnel hook, mounted on a cross-pin drill guide, is inserted through the tibial tunnel and into the femoral socket. A drill pin directed by the drill guide is drilled through the femur to intersect the femoral socket. The drill pin passes through the capture slot of the tunnel hook.

A hole then is formed in the femur, preferably using a cannulated drill placed over the guide pin, to accommodate a threaded section of the transtibial implant. A channel is formed in the lateral femoral cortex to accommodate the remainder of the implant, preferably using a dilator placed over the guide pin.

Next, a flexible strand, preferably a wire formed of nitinol, is attached to the guide pin and pulled through the femur. Equal lengths of the strand protrude from the medial and lateral sides of the femoral shaft, and are secured to prevent accidental pull-out. The tunnel hook is withdrawn, the strand being captured in the slot of the hook.

The hook is retracted completely, through the femoral socket and out of the tibial tunnel, such that a loop of the flexible strand protrudes from the entrance to the tunnel. Free ends of the strand remain exposed on either side of the femoral shaft.

The graft is passed through the diverted loop of the flexible strand. The loop is retracted into the femoral socket by pulling evenly on the medial and lateral ends of the strand. As a result, the graft is drawn into the socket.

The cannulated implant is placed over the wire and driven into the femur. The implant preferably is formed with back-biting threads. Accordingly, the implant easily can be impact driven into the repair site, and yet can be removed if necessary by rotation. The cannulated implant passes over the strand and under the tendon, thus securing the graft in the femoral socket.

Tibial fixation of the graft can be performed by various known methods, including interference screw fixation, which provides the most secure post-operative result; distal fixation with a cancellous screw using a post and washer technique; and a belt buckle staple technique utilizing a pair of ligament staples.

An alternative method of tendon loading is also provided for a closed-loop graft reconstruction. According to the alternative method, a flexible line is joined to one end of the strand. A strand/line loop is formed so as to protrude from the entrance to the tibial tunnel and present the junction between the strand and the line. The strand and the line are dejoined, opening the strand/line loop to accept the graft. The strand and line are rejoined so as to capture the graft, and the procedure continues substantially as set forth above.

Other features and advantages of the present invention will become apparent from the following description of the invention which refers to the accompanying drawings. For example, although the description herein relates to ACL grafts and forming femoral tunnels in the knee, it will become apparent that expanded indications for the inventive method include other joints and replacement of other ligament or tendon structures using various types of graft constructs.

DETAILED DESCRIPTION OF THE PREFERRED EMBODIMENTS

Figure 2:
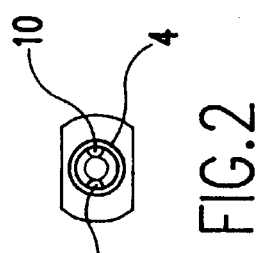
FIG. 2 is a distal end view of the tunnel hook of FIG. 1.
Figure 1:
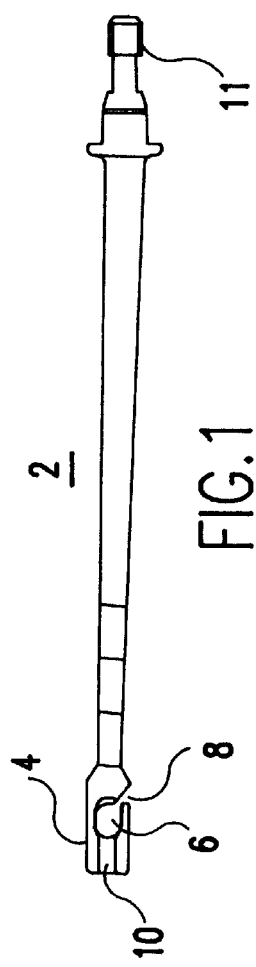
FIG. 1 is an elevation of a tunnel hook according to the present invention.

Referring initially to FIGS. 1 and 2, the present invention involves the use of a slim, longitudinal tunnel hook 2, which includes a shaft having a distal end and a proximal end. The distal end of tunnel hook 2 is provided with a hook 4, having a capture slot 6.

Various features of tunnel hook 2 are provided for ease of use in the inventive procedure of the present invention. The purpose of the following features will become more clear in light of the method described below. Angled opening 8 allows escape of a graft-passing wire from capture slot 6. Channels 10 on either side of hook 4 accommodate portions of the graft-passing wire as it forms a loop through a femoral tunnel. The proximal end of tunnel hook 2 features a mounting flange 11 for engagement with a drill guide.

Figure 5:
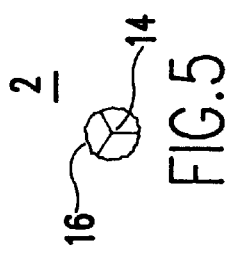
FIG. 5 is a distal end view of the drill pin of FIGS. 3 and 4.
Figure 3:
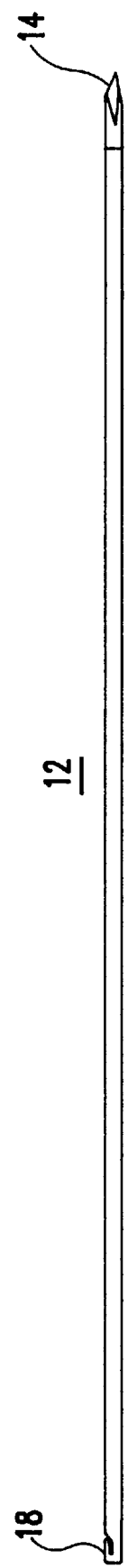
FIG. 3 is an elevation of a drill pin according to the present invention.
Figure 4:
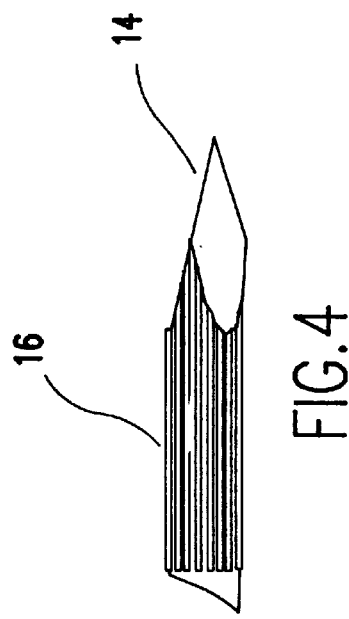
FIG. 4 is an enlarged view of the distal tip of the drill pin of FIG. 3.

Referring to FIGS. 3, 4, and 5, the invention also involves the use of a drill pin 12, which includes an elongated, narrow shaft having a pointed distal end and a proximal end. The distal end of drill pin 12 is provided with a sharp, trocar tip 14 and a fluted drilling region 16 disposed adjacent to and proximal the faces of trocar tip 14. The proximal end of drill pin 12 includes a hook 18 having an angled opening into its capture slot for engaging the graft-passing wire, as described more fully below.

Figure 6:
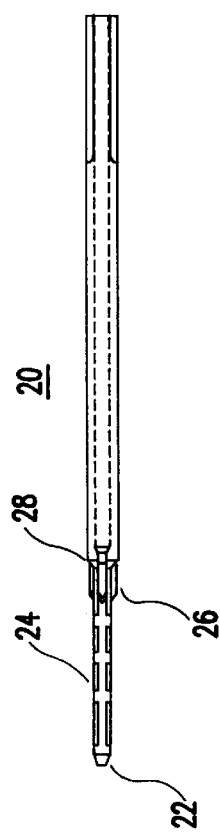
FIG. 6 is an elevation of a tunnel dilator according to the present invention.

Referring to FIG. 6, a tunnel dilator 20 is shown. Tunnel dilator 20 has a tapered distal end and a proximal end. Dilator 20 is cannulated to be received over drill pin 12. The dilator has an initial taper 22 at the distal end for insertion into the bone where the drill pin enters. A cylindrical portion 24 forms a channel in the femur for receiving an implant shaft. An interim fluted portion 26 can be provided alternatively to form a hole for receiving threads of the implant, as described below. A depth stop 28 is formed proximally.

Figure 7:
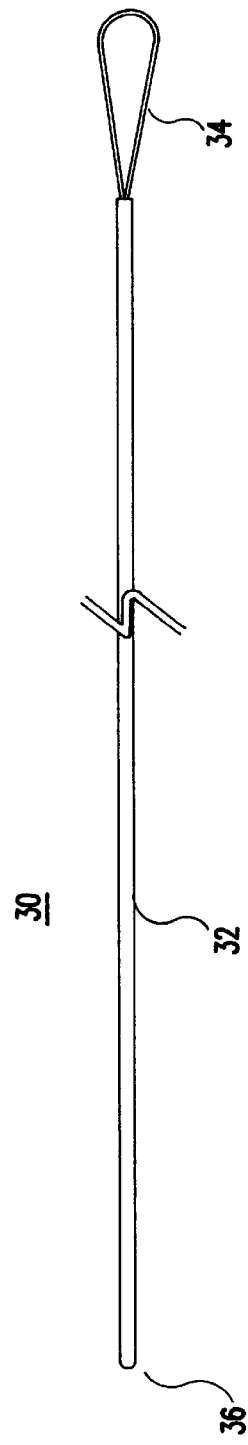
FIG. 7 illustrates a graft-passing wire according to the present invention.

Referring to FIG. 7, a nitinol graft-passing wire 30 is shown. Passing wire 30 includes a flexible portion 32 having a loop 34 formed on the distal end and a rounded proximal end 36.

Figure 8:
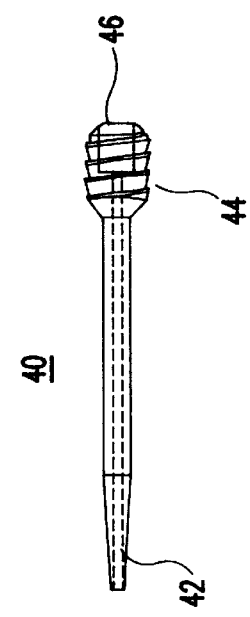
FIG. 8 illustrates a transverse implant having back-biting threads according to the present invention.
Figure 9:
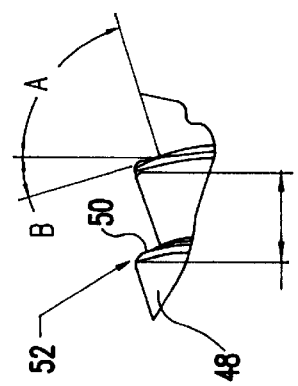
FIG. 9 is an enlarged detail view of the back-biting threads of the transverse implant illustrated in FIG. 8.
Figure 10:
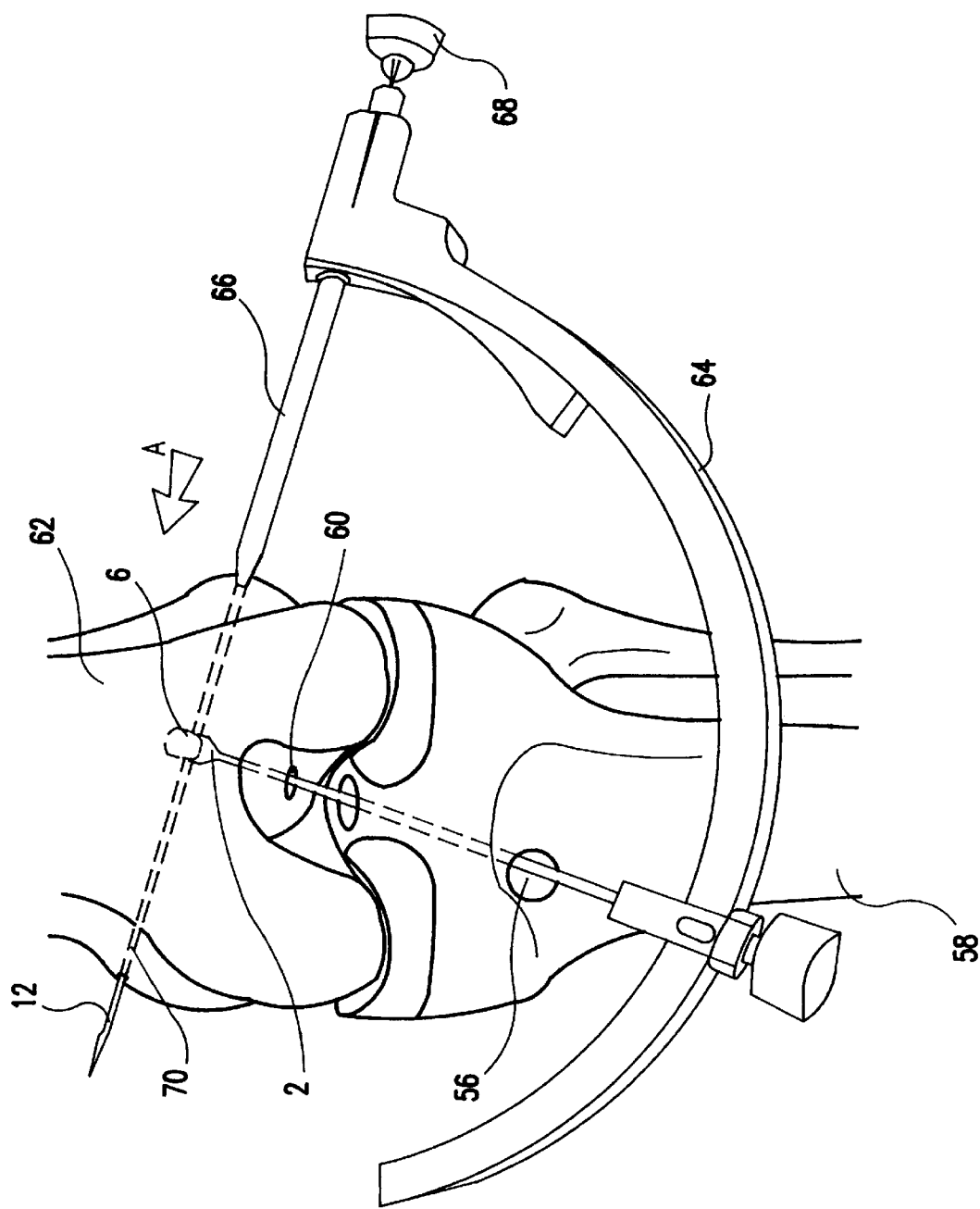
FIG. 10 is a schematic view of a hook and a drill pin mounted on a drill guide and disposed within the femoral socket according to the present invention.

FIGS. 8 and 9 illustrate a transverse implant 40. Implant 40 has a threaded proximal end and a threaded distal ends. The implant is cannulated to be received over graft-passing wire 30. The implant has a taper 42 formed toward the distal end. The proximal end includes back-biting, helical threads 44 and a drive socket 46. As shown in detail in FIG. 9, threads 44 have a sloping distal face 48 and a proximal face 50 meeting at a radiused edge 52. Distal face 48 forms an angle A of about 72° with a perpendicular to the central axis of the implant. Proximal face 50 forms an angle B of about 18° with the perpendicular. The implant can be driven by impaction into bone, and then, if necessary, can be subsequently removed by screw rotation as discussed below.

The method of the present invention is described with reference to FIGS. 10 through 16. A longitudinal tibial tunnel 56 is formed using known techniques of drilling up through the tibia 58. Reproducible tunnel placement is achieved using instruments that reference intra-articular anatomical constants. A cannulated drill, received over a guide, is used to drill the tibial tunnel. Depending on the size of the graft, tunnel diameters of 7, 8, 9, and 10 mm are can be used.

Once the tibial tunnel is formed, a cannulated headed reamer is used to form a closed-ended socket 60 in the femur 62. The socket is formed to a minimum depth of about 40 mm to accommodate the insertion depth of tunnel hook 2. The knee should be placed in 90° of flexion when forming the tibial tunnel and femoral socket.

The tunnel and socket can be modified in various ways using tunnel taps. For example, crenulations formed in the tibial tunnel provide additional friction and helps eliminate unwanted graft rotation during interference screw insertion. A spiral groove formed in the tunnel wall provides additional interference friction of the graft collagen against the compressed cancellous bone in the tunnel. A rasp may be used to create an oval-shaped tunnel and femoral socket to accommodate insertion of four tendon strands.

After the tibial tunnel and femoral socket are complete, tunnel hook 2, fitted onto a C-ring cross-pin drill guide 64, is inserted through tibial tunnel 56 and into femoral socket 60. Tunnel hook 2 will capture within slot 6 the graft-passing wire 12 used in loading the graft tendons into the femoral socket, as described below with respect to FIGS. 12 and 13.

Referring again to FIG. 10, with tunnel hook 2 and drill guide 64 in place, a 2 mm drill pin sleeve 66 is advanced in the direction of arrow A up to the skin proximal to the femoral condyle to indicate an incision site. The drill guide is positioned to allow the pin to pass parallel to the coronal plane, without excessive posterior or anterior divergence. A 2-cm incision is made transversely at this site through the skin and fascia lata, and soft tissue is cleared down to the condyle. Drill pin sleeve 66 is advanced until it contacts bone. Over-tightening of the drill pin sleeve against the femoral cortex is avoided to prevent the drill pin from deviating and missing capture slot 6 of tunnel hook 2. A depth indicator on the sleeve is used to gauge the length of implant 40 that will be required.

With the sleeve in position against the cortical bone, drill pin 12, 2 mm. in diameter, is chucked into a power drill 68, and advanced with rotation through the femur until it exits the skin on the medial side 70. To ensure that the drill pin passes within the capture slot 6 of tunnel hook 2, torque on the drill guide and changes in knee flexion are avoided during drilling.

Figure 11:
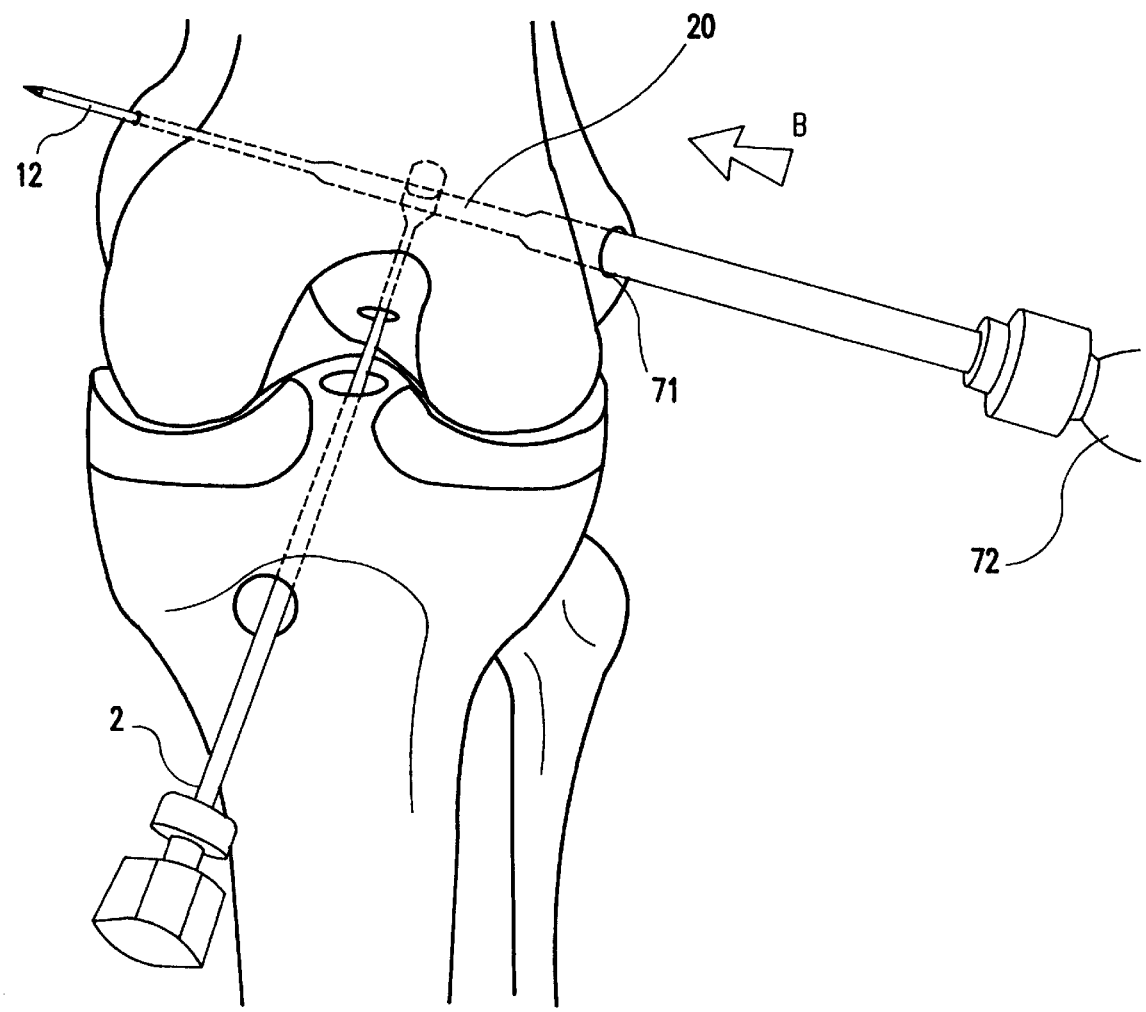
FIG. 11 is a schematic view of a tunnel dilator being used to form a femoral channel for the transverse implant according to the present invention.

Referring to FIG. 11, a cannulated drill is placed over the guide pin to drill a hole 71 to accommodate threaded section 44 of implant 40. The drill is replaced with tunnel dilator 20, which is used to form a channel in the femur for the remainder of implant 40. Tunnel dilator 20 is mounted onto a driver/extractor 72 and driven with a mallet in the direction of arrow B up to a depth stop (not shown).

Figure 12:
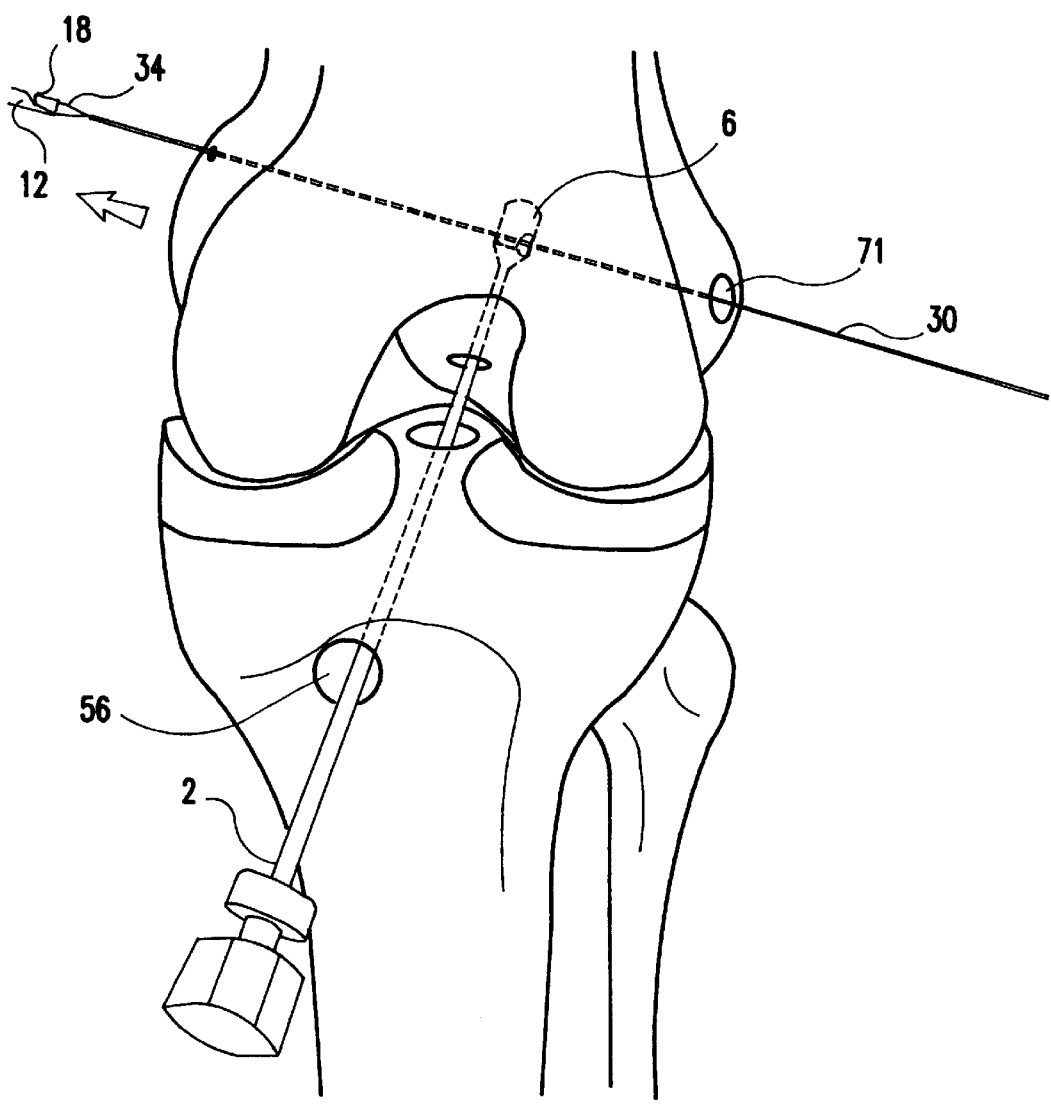
FIG. 12 illustrates a flexible strand attached to the drill pin and being pulled through the femur according to the present invention.

Referring to FIG. 12, once the channel has been formed, loop 34 of nitinol graft-passing wire 30 is hooked onto hook 18 on the proximal end of drill pin 12. By pulling on the drill pin, the graft-passing wire is drawn through the femur until it is positioned with equal lengths at either end protruding from the medial and lateral sides of the femoral shaft.

Figure 14:
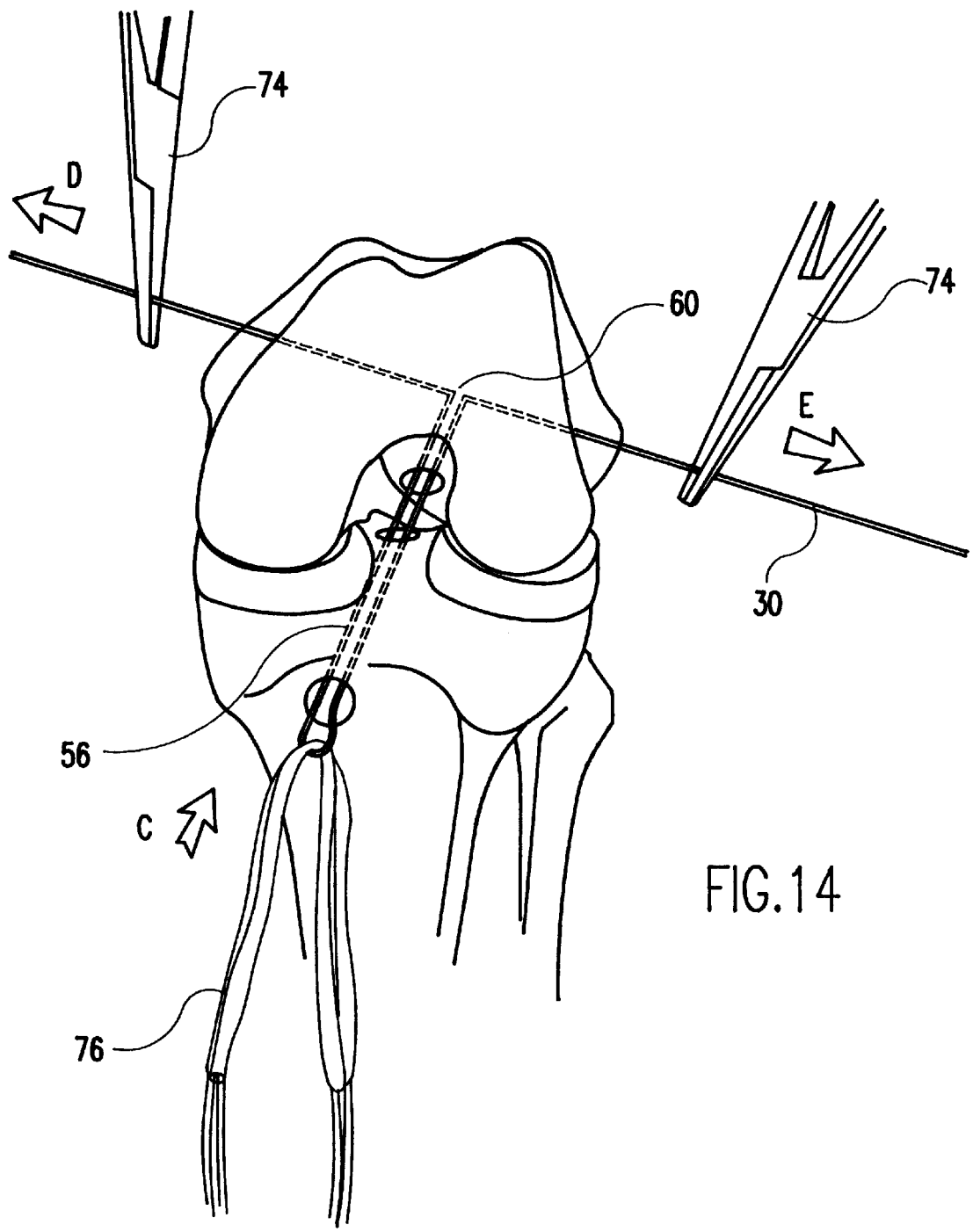
FIG. 14 illustrates the flexible strand loop having been diverted through the tibial tunnel, capturing a ligament graft, and pulling the graft into the tibial tunnel according to the present invention.

Hemostats 74 are clipped onto the ends of the wire to prevent them from being pulled into the transverse femoral tunnel 70, as shown in FIG. 14.

Figure 13:
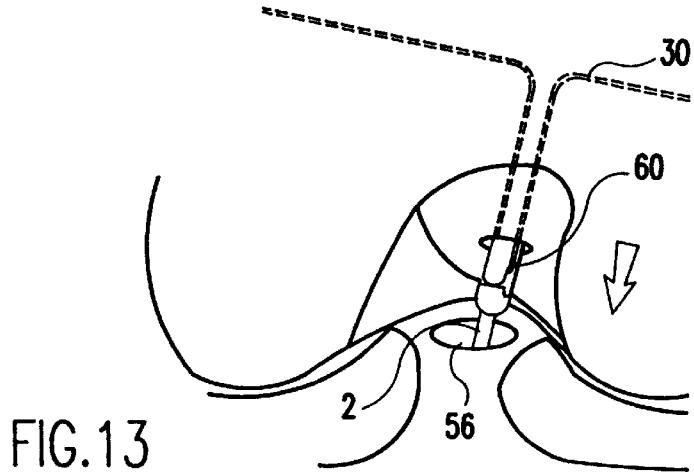
FIG. 13 illustrates a loop of the flexible strand being pulled by the hook and out through the femoral socket according to the present invention.

Referring to FIGS. 13 and 14, once the graft-passing wire has been drawn through the femur, tunnel hook 2 is retracted from femoral socket 60 and tibial tunnel 56, pulling graft-passing wire 30 with it to form a loop that protrudes from the entrance of tibial tunnel 56 on the anterior tibial cortex. The semitendinosus and gracilis tendons 76 are placed evenly over the wire loop, and the loop containing the tendons is retracted in the direction of arrow C back through the tibial tunnel and into the femoral socket by pulling evenly on the medial and lateral ends of the graft-passing wire, as shown by arrows D and E, respectively. Twisting of the graft during insertion is avoided.

Figure 15:
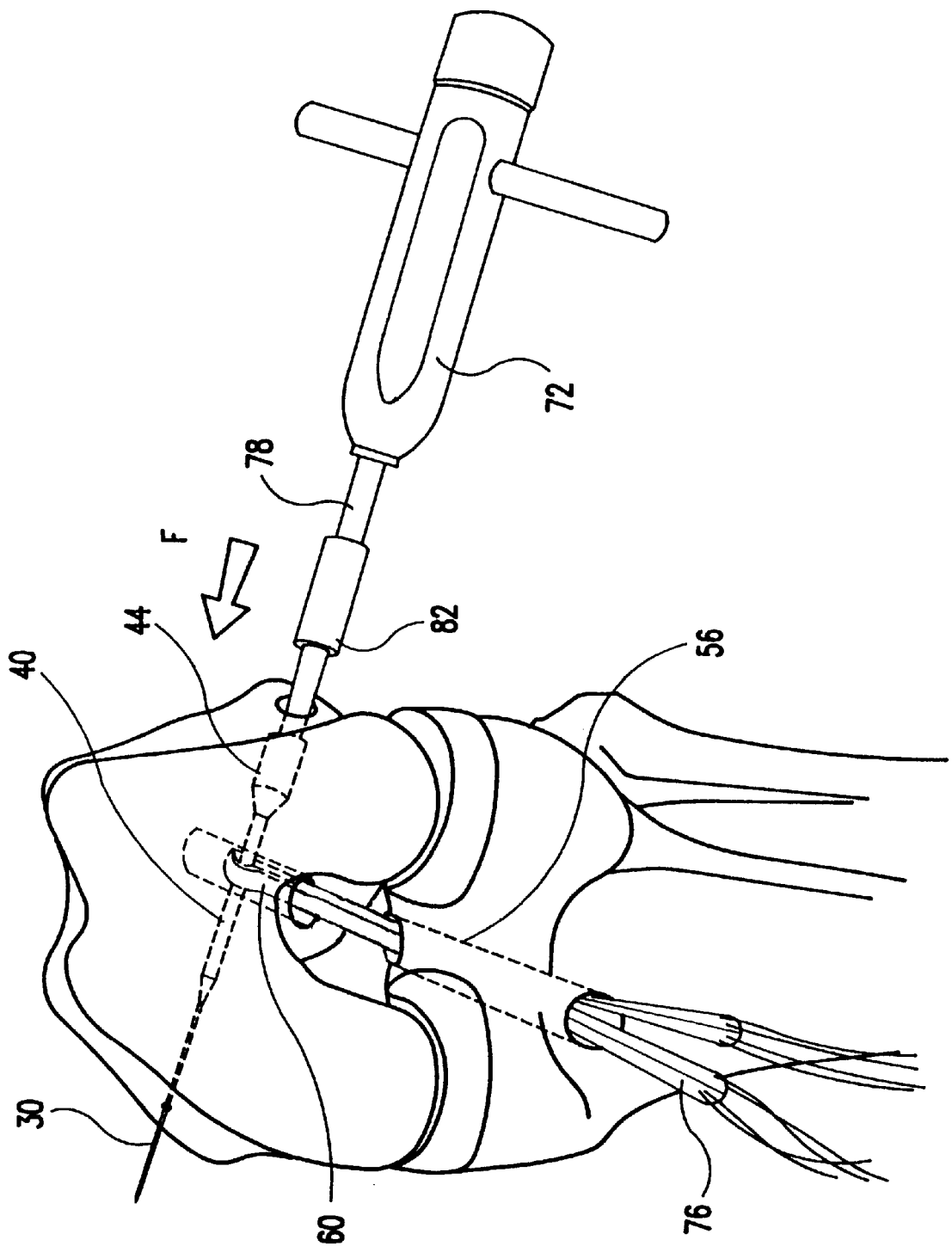
FIG. 15 illustrates the ligament graft, having been loaded through the longitudinal tibial tunnel and into the femoral socket, being fixated using a transverse implant according to the present invention.

Referring to FIG. 15, once the tendons 76 have been drawn completely into femoral socket 60, implant 40 is inserted over the guide wire and advanced by hand until the threaded section 44 contacts the femur. An implant impactor 78 is chucked into driver/extractor 72 and placed over the wire 30. The head of the implant 40 is engaged and a mallet is used to drive the implant into the femur until a depth stop 82 on the driver 78 contacts the cortical bone. Pulling on the tendons 76 is avoided during impaction of the implant 40.

The implant is advanced along the wire in the direction of arrow F. The implant passes under the loop formed in tendons 76, toward the medial side of the femur, to provide cross-pin support of tendons 76. If removal of the implant should become necessary, reverse cutting threads 44 facilitate removal by unscrewing the implant with a 3.5 mm hex head screwdriver.

Figure 16:
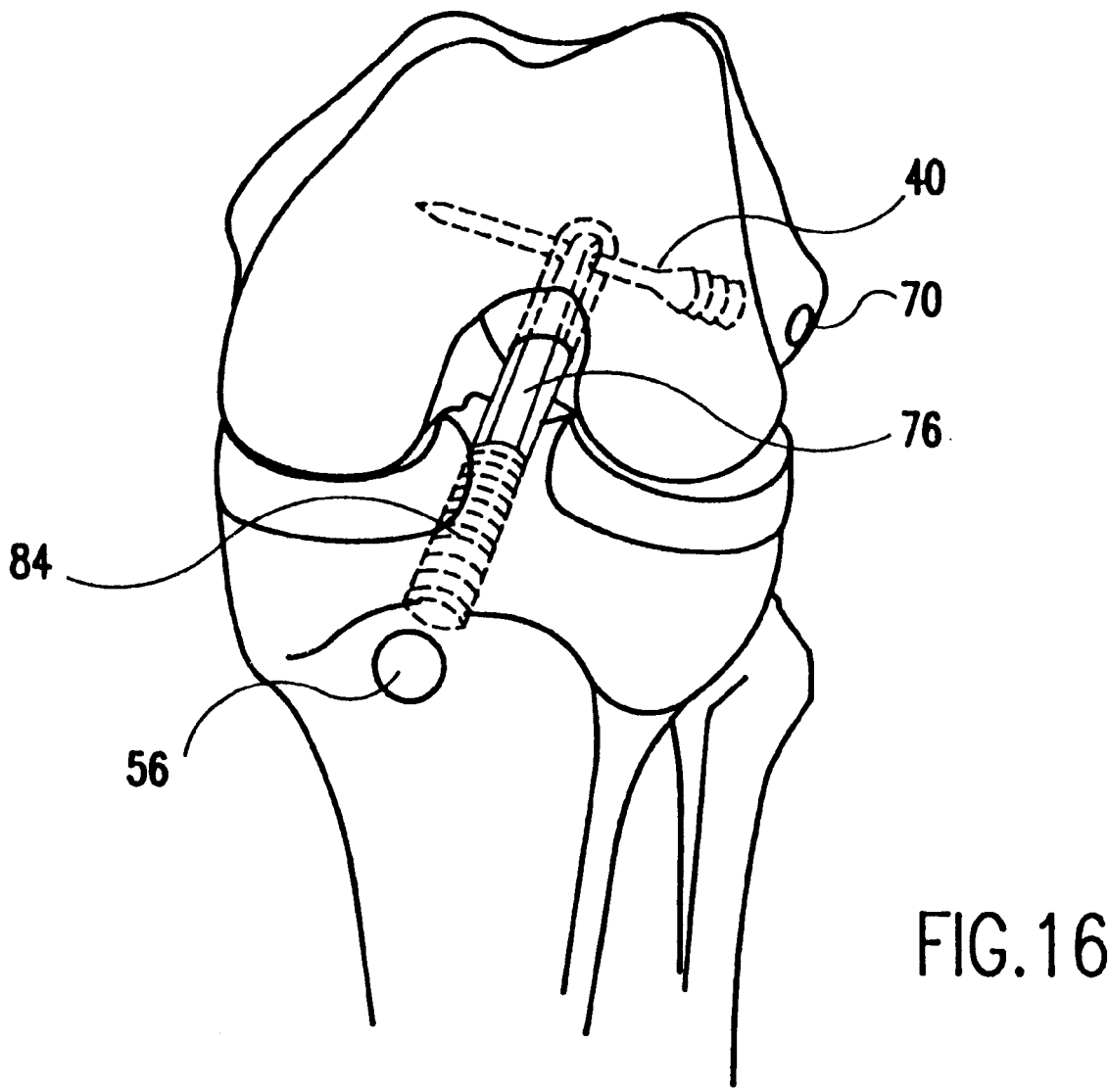
FIG. 16 illustrates a completed tendon graft repair including tibial fixation with an interference screw.

Referring to FIG. 16, the repair is completed by interference screw 84 fixation of graft 76 in tibial tunnel 56. The femoral tunnel is narrow so that tendons 76 fit snugly within tibial tunnel 56 and femoral socket 60, thus avoiding wiping of the tendons along the implant.

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed is:

1. A method of surgery, comprising the steps of:
    forming a socket in a bone, the socket having an entrance and a sidewall;
    introducing a flexible strand transversely into the socket through the sidewall of the socket;
    pulling a portion of the strand out through the socket entrance;
    engaging a graft with the portion of the strand pulled out of the socket entrance; and
    pulling the flexible strand and the graft engaged thereto into the socket.

2. The method of claim 1, wherein the step of pulling a portion of the strand out through the socket entrance is followed by a step of forming a loop in the strand outside the entrance to the socket for engaging the graft.

3. The method of claim 2, further comprising the steps of:
    opening a junction in the strand loop pulled outside the entrance to the socket to form two free ends; and
    reforming the loop by reattaching the two free ends so as to capture a graft within the reformed loop.

4. The method of claim 1, wherein the step of pulling a portion of the strand out through the socket entrance comprises engaging the strand with a hook.

5. The method of claim 4, wherein the step of pulling a portion of the strand out through the socket entrance further comprises the step of inserting the hook into the socket and retracting the hook and the strand engaged thereto from the socket.

6. The method of claim 5, wherein the hook is inserted into the socket prior to introducing the flexible strand into the socket.

7. The method of claim 1, further comprising the step of forming a loop in the graft and engaging the loop in the graft with the portion of the strand pulled out through the socket.

8. The method of claim 1, further comprising the step of supporting the graft in the socket.

9. The method of claim 8, wherein the step of supporting the graft in the socket is performed using a transverse implant.

10. The method of claim 9, wherein the implant is cannulated, the method further comprising the step of guiding the implant using the strand.

11. The method of claim 1, wherein the flexible strand comprises wire.

12. A surgical method, comprising the steps of:

forming a socket in bone, the socket having an entrance and a sidewall;

introducing a hook having an eye into the socket;

drilling a guide pin through the sidewall of the bone socket so as to transversely intersect the socket, the guide pin passing through the eye of the hook;

pulling a flexible strand transversely through the bone socket using the guide pin;

pulling a loop in the flexible strand out through the entrance of the socket using the hook;

engaging a tendon graft with the loop in the flexible strand pulled out of the entrance of the socket;

pulling the flexible strand in a direction transverse to the socket so as to draw the graft engaged therewith into the socket; and supporting the graft within the socket.

13. The method of claim 10, wherein the step of supporting the graft comprises passing an implant transversely through a loop formed in the graft in the socket.

14. The method of claim 13, wherein the implant is cannulated.

15. The method of claim 12, wherein the flexible strand comprises wire.

* * * * *